United States Patent [19]

Lo et al.

[11] Patent Number: 4,548,473
[45] Date of Patent: Oct. 22, 1985

[54] OPTICAL FILTER

[75] Inventors: Sau K. Lo, Fridley; Ronald E. Peterson, Shoreview, both of Minn.

[73] Assignee: Honeywell Inc., Minneapolis, Minn.

[21] Appl. No.: 493,850

[22] Filed: May 12, 1983

[51] Int. Cl.$^4$ .............................................. G02B 5/20
[52] U.S. Cl. ................................... 350/311; 252/582
[58] Field of Search ............... 350/311, 312; 252/582, 252/584, 587, 588, 589

[56] References Cited

U.S. PATENT DOCUMENTS

| | | |
|---|---|---|
| 3,062,103 | 11/1962 | Bolz . |
| 3,190,172 | 6/1965 | Langberg . |
| 3,458,249 | 7/1969 | George ................................ 350/312 |
| 3,519,339 | 6/1970 | Hutchinson et al. . |
| 3,792,916 | 2/1974 | Sarna . |
| 4,070,101 | 1/1978 | Richards et al. . |

OTHER PUBLICATIONS

Schmidt, R. N. et al., "Application of Mie Scatter Theory to the Reflectance of Paint-Type Coatings", Appendix A of ASME Fourth Symposium on Thermophysical Properties, 1968.

Primary Examiner—Bruce Y. Arnold
Attorney, Agent, or Firm—William T. Udseth

[57] ABSTRACT

An optical filter comprising a first substance which is substantially transparent to light within a selected first frequency range and having a first index of refraction; and a second substance which has at least one resonance frequency within said first frequency range and having a second index of refraction which is substantially the same as said first index of refraction at all of the frequencies within said first frequency range except for frequencies near said resonance frequency.

5 Claims, 5 Drawing Figures

OPTICAL FILTER

BACKGROUND OF THE INVENTION

1. Field of the Invention

This invention relates to means and methods for filtering selected wavelengths by resonant scattering. More particularly the invention relates to filtering selective wavelengths by mismatching the index of refraction of a host material and a scattering-absorbing material.

2. Prior Art

Numerous optical filters, including filters for protecting against laser radiation have been disclosed. For example Hutchinson, et al in U.S. Pat. No. 3,519,339 discloses protective laser goggles comprised of front and rear glass plates for respectively absorbing ultraviolet light and infrared light, and including sandwiched therebetween two separate multilayer dielectric coatings made up of high and low index of refraction materials to define a narrow pass band of visible light which is different from the wavelength of a particular laser light.

Sarna in U.S. Pat. No. 3,792,916 discloses a filter assembly for selectively removing individual emission lines of laser energy from the visible spectrum comprising at least one pair of Fabry-Perot filters which transmit laser energy emissions for dissipation in the filter assembly and reflect harmless radiation for transmission through the assembly.

Richards, et al in U.S. Pat. No. 4,070,101 discloses a wide angle narrow bandpass optical filter including multiple absorption materials in a common path. Langberg in U.S. Pat. No. 3,190,172 employs a transparent scattering cell containing sodium vapor. The absorption of spectral radiation produces a resonance radiation (i.e., the absorption of photons of a specific wavelength and the re-emission of photons of the same or other wavelengths) within the cell.

The standard Christiansen filter is comprised of two materials which have different dispersion curves that intersect at one point. At the intersection, the indices of refraction of the materials is the same and the filter transmits light at the frequency corresponding to the point of intersection with little loss, while significantly scattering light at other frequencies.

Problems remain with all the prior art filters. First, it is difficult to obtain a sufficiently narrow absorption band in an absorption filter, so that out-of-band transmissions are high enough to not compromise the effectiveness of optical equipment or an operator of a device. Second, prior art filters are relatively large, of fixed configuration and relatively rigid. This implies difficulty in integrating the filter into most existing optical elements. Third, it is desirable to increase the hardness to laser radiation of prior filters without materially increasing size or complexity.

Theoretical calculations using Mie scattering theory have been made for three dimensional scattering in paint coatings due to small spherical scattering particle dispersed in the coating. The results are published in "Application of Mie Scatter Theory to the Reflectance of Paint-Type Coatings", R. N. Schmidt, P. M. Treaenfals and E. J. Meeham Proceedings of the ASME Fourth Symposium on Thermophysical Properties, 1968 at p. 256 and are incorporated herein by reference.

FIG. 1 is qualitative graph illustrating some general conclusions of the Schmidt, et al report. In FIG. 1, Ks is a scattering coefficient which is a partial measure of the influence of a particle in a paint coating on light incident on the coating. Ks is a measure of the scatter of light striking such a particle. Ks is defined as: assuming energy of uniform intensity is incident on a particle and surrounding area, it is the ratio of energy scattered (i.e, deviated by reflection or refraction) to that going through an area equal to the geometrical cross-section of the particle. The ratio of particle radius to wavelength is represented by $\alpha$, where:

$$\alpha = \frac{2\pi R_g}{\lambda} \quad (1)$$

where $\lambda$ is the wavelength in the surrounding media and $R_g$ is the geometrical radius of the particle.

FIG. 1 is plot of Ks versus $\alpha$ (shown as line 10) with the index of refraction no of the host material equal to a constant Q. Two peaks 12 and 14 are shown as well as points 16 and 18. Assuming $\lambda$ is fixed, between the origin O and the value of $\alpha$ corresponding to the first peak 12 (i.e., $\alpha$ 1) a smaller $\alpha$ implies a smaller $R_g$ particle. This is shown by noting that $\alpha$ 2 corresponding to point 16 is larger than $\alpha$ 3 corresponding to point 18.

As $R_g$ becomes larger (i.e., generally as $\alpha$ exceeds $\alpha$ 1) the Schmidt, et al paper discloses that scattering is shifted from predominately side scatter to predominately forward scatter. The Schmidt, et al paper was concerned with properties of reflecting paint coatings. The present invention discloses a new optical filter based upon Mie scattering theory.

SUMMARY OF THE INVENTION

The present invention is an optical filter comprising: a first substance which is substantially transparent to light within a selected first frequency range and having a first index of refraction, and a second substance having at least one resonance frequency within the first frequency range and a second index of refraction which is substantially the same as the first index of refraction at all the frequencies within the first frequency range except for frequencies near the resonance frequency.

The preferred embodiment provides that the second substance is formed into submicron size discs having a radius approximately equal to the wavelength corresponding to the resonance frequency divided by the index of refraction of the first substance times two.

PREFERRED EMBODIMENT

An optical filter 20 (see FIG. 2) is provided by a first substance 22 (i.e, a host substance) having an index of refraction no and which is substantially transparent to light of a selected frequency range. Located within substance 22 is a second substance 24 (shown as spherical particles in FIG. 1) which has a second index of refraction $n_S$. Substance 24 has at least one resonance frequency within the selected frequency range. Ns is substantially the same as $n_o$ for frequencies within the selected frequency range except for frequencies at which the second substance exhibits substantial dispersion.

Resonance frequency as used herein means the effective resonance frequency of bound electrons in a dielectric material given by:

$$\omega_o = \sqrt{\frac{B}{m} - \frac{Ne^2}{3\epsilon_o m}} \quad (2)$$

where N equals the number of electrons per unit volume, B is the force constant due to an electron being elastically bound to its equilibrium position in the dielectric material, e is the charge on an electron, m is the mass of an an electron, and $\epsilon_o$ is the permittivity of free space. Equation 2 is derived in the literature assuming an isotropic medium and that all electrons are identically bound. It is sufficient for the general discussion of the present invention although those skilled in the art will recognize that appropriate modifications would be made for specific substances and for further refinements depending on the needs and wishes of those employing the present invention.

Figure 3:
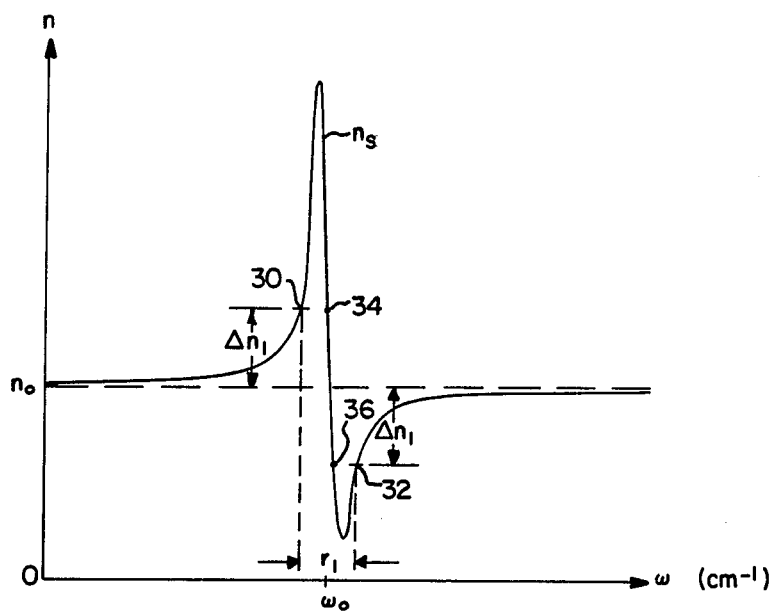
FIG. 3 is a graph of the index of refraction of a host material and scattering particles dispersed within the host material as a function of the frequency of light incident on the host material.

FIG. 3 shows $n_o$ and $n_s$ as a function of the frequency $\omega$ of incident light 26 (see FIG. 1) which strikes surface 28 of device 20.

FIG. 3 includes a typical, qualitative plot of resonance frequency demonstrating both normal and anomalous dispersion. Normal dispersion is an increase of $n_s$ above a nominal value (the nominal value being approximately equal to $n_o$) as the frequency approaches $\omega_o$ and anomalous dispersion is a decrease in $n_s$ from a nominal value as the frequency becomes slightly larger than $\omega_o$.

The difference between $n_o$ and $n_s$ (i.e., $\Delta n$) for two specific points 30 and 32 (one on each side of frequency $\omega_o$) is shown as $\Delta n_1$. The range of frequency between points 30 and 32 is $r_1$. Note that the difference between points 34 and 36 and $n_o$, respectively, is also equal to $\Delta n_1$.

Figure 4:
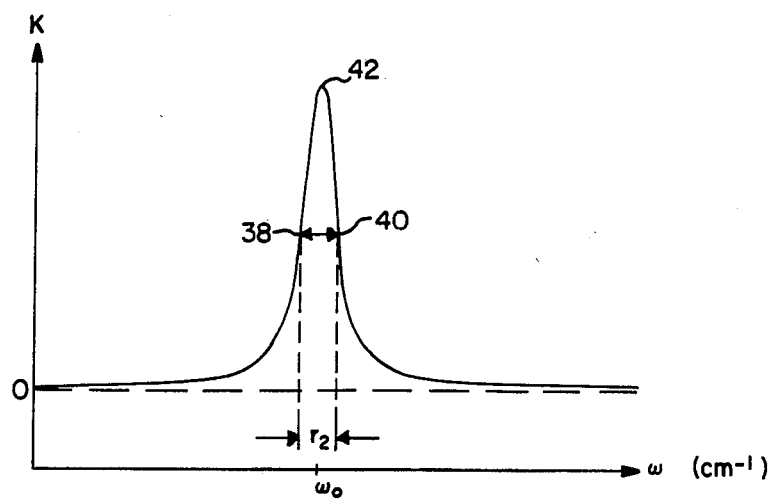
FIG. 4 is a graph of the extinction coefficient as a function of frequency for a filter comprised solely of the scattering-absorbing material.

FIG. 4 is a plot of the extinction coefficient k of substance 24 as a function of frequency. Points 38 and 40 indicate the full width and half maximum of peak 42. Range $r_2$ is the frequency range spanned by the full width half maximum. FIG. 4 indicate strong absorption of light at frequencies near $\omega_o$. In fact, maximum absorption occurs at precisely $\omega_o$.

Assuming the frequency range of interest is the frequency scale on the abscissa of FIG. 3, it is seen that $n_o$ and $n_s$ are substantially the same at all frequencies within the range of interest except for frequencies where dispersion is exhibited. Note that $n_o$ equals $n_s$ at $\omega_o$. Substantial scattering of incident light will occur only at frequencies where a substantial deviation occurs between $n_s$ and $n_o$, i.e., where $\Delta n$ is substantial. The definition of substantial for purposes of determining $\Delta n$ will vary with the particular applications of the present invention. Frequency ranges where $\Delta n$ is substantial will define frequencies which are near the resonance frequency.

Figure 2:
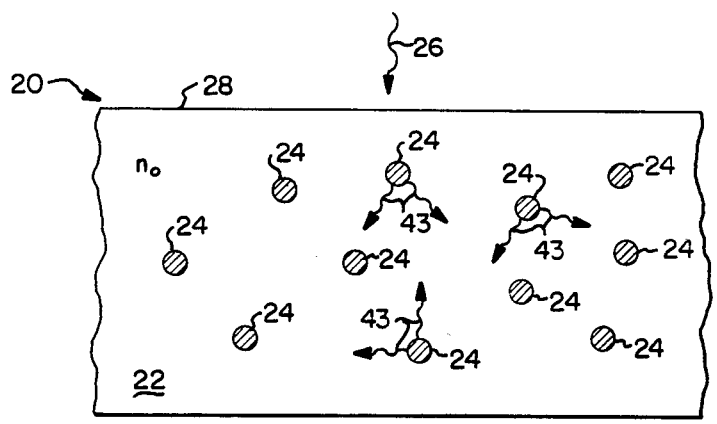
FIG. 2 is a schematic of a device in accordance with the present invention.

For purposes of illustration, and for many expected applications of present invention, $\Delta n$ can be significant when it exceeds 0.5 . From FIG. 3, it is thus seen that substantial scattering of incident light 26 will occur when the frequency of the incident light falls between points 30 and 34 and between points 32 and 36. Note however, due to the very strong absorption between points 34 and 36, that the net effect of both scattering and absorption is to produce significant attenuation of incident light having a frequency between points 30 and 32. Scattered light 43 which is scattered from substance 24 is illustrated in FIG. 2.

Figure 1:
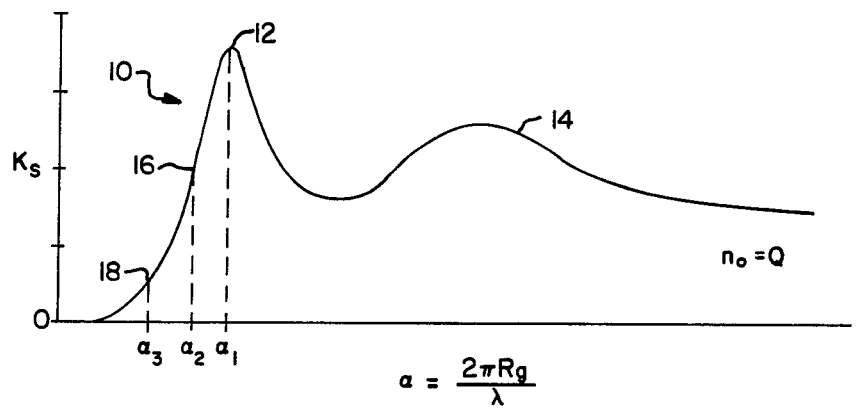
FIG. 1 is a schematic of the scattering coefficient of particles in a reflecting paint coating as a function of the size of the particles and the wavelength of light incident on the paint coating.

As indicated above with respect to FIG. 1, some directivity is imposed on the scatter angle due to particle size. It is thus preferable to provide a particle 24 having Rg given by:

$$R_g \sim \frac{\lambda_o}{2n_o} \quad (3)$$

where $\lambda_o = C/\omega_o$. This will place Rg approximately at the first peak of FIG. 1 thus maximizing the scatter coefficient Ks. Note that equation 3 is only an approximation and is most accurate when there is a substantial difference between $n_s$ and $n_o$ in the frequency range where dispersion occurs (i.e, $\Delta n$ is at least 2.0 as a maximum value). If one is constrained to choose values of Rg other than the approximate preferred value, it is generally preferable to choose Rg slightly smaller than the value given by equation 3 because of the directivity imposed on the scatter angle discussed above.

The preferable shape of the scatter particle 24 is a disc, with the flat surface of the disc being oriented perpendicular to the expected direction of the incident light. The circular surface of the disc should be of radius Rg. The disc shape is preferable to a sphere of similar radius since it is expected that it will maximize the nonforward scattering of incident light. For many applications however, it may be much easier to form particles 24 as spheres therefore the precise shape of the particles is highly dependent on the particular application and cost for obtaining suitable particles.

Resonant scattering near the absorption peak enhances the attenuation of the desired spectral frequency in two ways. First, due to nonforward scattering, transmitted electromagnetic radiation is reduced. Second, through nonforward scattering, the optical path of electromagnetic radiation through an absorbing substance (such as substance 24) would be dramatically increased. Multiple scatterings from particles 24 of course increase both the above effects. The transmission curve of device 20 as a function of frequency is the complement of the Christiansen filter.

Furthermore, the extinction band of device 20 can be narrowed relative to the absorption band of substance 24 alone, by distributing substance 24 as scattering particles in accordance with the present invention. This is because substantial scattering occurs only over portions of the range $r_1$ as discussed above. If $r_1$ is less than the full width half maximum (i.e., $r_1 < r_2$) substantial scattering will take place over a smaller range than the range over which substantial absorption would occur due to a pure substance 24. This implies that for frequencies within $r_2$ but outside of $r_1$, the only mechanism attenuating incident light is the absorption mechanism due to substance 24. However, since device 20 disperses absorbing-scattering substance 24 throughout a host substance 22 which is predominately transparent to all frequencies of interest, little absorption will take place for light of frequencies within $r_2$ but which lie outside $r_1$. And, since the scattering phenomenon is insubstantial for frequencies outside $r_f$, the net effect will be an extinction band which is approximately coextensive with $r_f$ and sharply defined by $r_1$, relative to the absorption band due to material of substance 24 alone.

Device 20 is projected to provide 100 times more attenuation than is possible with a filter comprised of substance 24 alone. It is further possible that attenuation could be enhanced by as much as 1000 times.

Figure 5:
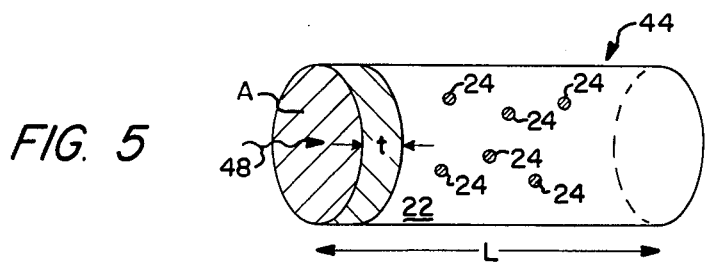
FIG. 5 is a model for comparing the effectiveness of a device in accordance with the present invention to the filter of FIG. 4.

An approximation of the enhanced attenuation can be obtained from examining FIG. 5. A hypothetical circular cylinder 44 with cross section of area A and length L is shown. Cylinder 44 is a "plug" extracted from device 20. The volume of substance 24 within cylinder 44 would form a disc 46 of area A and thickness t. The attenuation of device 20 with a volume of substance 24 equal to Axt disposed throughout host substance 22 as particles 24, would be larger than the attenuation due to the volume of substance 24 formed as disc 46 for incident light 48. The larger attenuation would be on the scale discussed above.

Preferably neither host substance 22 nor scattering substance 24 will absorb the other substance. It is further preferable to infuse scattering substance 24 directly into host substance 22 without encapsulation. Those skilled in the art will recognize the dispersion characteristics of substances suitable for scattering light at only those wavelengths of interest for a particular application. However, metalloprophyrin organic dyes are potentially adaptable for use as scattering materials for frequencies in the visible range, as is inorganic material $CaF_2$ with F centers.

Polyvinyl alcohol, glass and various plastics are examples of some materials potentially adaptable as host substance 22.

Submicron polystyrene spheres, injected with a thioxanthene dye is an encapsulation method which can be employed, with the spheres embedded or suspended in host substance 22. One possible host is a fluid of benzoalcohol aniline saturated with polystyrene prior to suspension of the spheres therein.

Due to the enhanced attenuation of device 20 a coating only a few hundred microns thick could provide sufficient filtering of unwanted frequencies for many applications. This in turn, allows the present invention to conform to complex surfaces and be readily integrated into many existing optical elements at relatively low cost. At the same time, the high transmissivity for out-of-band wavelengths allows equipment or operators to receive nearly all incident out-of-band light. Further, device 20 is intrinsically harder to laser radiation that conventional absorbing material because significant amounts of incident radiation are scattered in addition to the radiation absorbed by the substances found in device 20.

What is claimed is:

1. An electromagnetic energy filter comprising:
    a first substance which is substantially transparent to electromagnetic energy within a selected first frequency range and having a first index of refraction;
    a second substance having at least one resonance frequency within said first frequency range and having a second index of refraction which is substantially the same as said first index of refraction at all of the frequencies within said first frequency range except for frequencies near said resonance frequency, wherein said second substance is comprised of particles located, at least in part, within said first substance; and
    wherein said particles have a maximum dimension of approximately $\lambda/2n$, where $\lambda$ is the wavelength of light in said first substance with frequency equal to said resonance frequency and n is said first index of refraction.

2. A method of filtering electromagnetic energy of substantially a selected frequency from incident electromagnetic energy, comprising:
    providing a first substance which is substantially transparent to electromagnetic energy within a selected first frequency range and having a first index of refraction;
    providing a second substance which has at least one resonance frequency within said first frequency range and having a second index of refraction which is substantially the same as said first index of refraction at all of the frequencies within said first frequency range except for frequencies near said resonance frequency;
    forming said second substance into particles having a maximum dimension of approximately $\lambda/2n$, where $\lambda$ is the wavelength of light in said first substance with frequency equal to said resonance frequency and n is said first index of refraction,
    placing said particles, at least in part, within said first substance, and
    irradiating said first substance with said incident light.

3. A coating for glass or plastic optical elements for filtering electromagnetic energy, comprising:
    a first substance which is substantially transparent to electromagnetic energy within a selected first frequency range and having a first index of refraction;
    a second substance having at least one resonance frequency within said first frequency range and having a second index of refraction which is substantially the same as said first index of refraction at all of the frequencies within said first frequency range except for frequencies near said resonance frequency, wherein said second substance is comprised of particles located, at least in part, within said first substance, and
    wherein said first and second substances can, in combination, be applied as a coating which will adhere and conform to selected surfaces of said optical elements.

4. The coating of claim 3 wherein said combination has a thickness of less than 1000 angstroms.

5. A method of filtering electromagnetic energy with glass or plastic optical elements, comprising:
    providing a first substance which is substantially transparent to electromagnetic energy within a selected first frequency range and having a first index of refraction;
    combining said first substance with a second substance comprised of particles, wherein said second substance has at least one resonance frequency within said first frequency range and a second index of refraction, with said second index of refraction being substantially the same as said first index of refraction at all of the frequencies within said first frequency range except for frequencies near said resonance frequency, said particles being located, at least in part, within said first substance, said combination being capable of adhering to and conforming to surfaces of said optical elements; and coating at least a portion of the surface of said optical elements with said combination.

* * * * *